United States Patent [19]

Kung

[11] Patent Number: 5,278,308
[45] Date of Patent: Jan. 11, 1994

[54] IODINE DERIVATIVES OF TETRABENAZINE

[75] Inventor: Hank F. Kung, Wynnewood, Pa.

[73] Assignee: The Trustees of The University of Pennsylvania, Philadelphia, Pa.

[21] Appl. No.: 843,041

[22] Filed: Feb. 28, 1992

[51] Int. Cl.$^5$ .......................................... C07D 455/06
[52] U.S. Cl. ...................................................... 546/95
[58] Field of Search ........................... 546/95; 424/1.1

[56] References Cited

U.S. PATENT DOCUMENTS

| | | | |
|---|---|---|---|
| 3,053,845 | 9/1962 | Tretter | 546/95 |
| 3,314,966 | 4/1967 | Brossi et al. | 546/95 |
| 3,393,198 | 7/1968 | Unger et al. | 546/95 |

OTHER PUBLICATIONS

Brossi, et al., "16. Syntheseversuche in der Emetin Reihe 1. Mitteilung 2-Oxo-hydrobenzo[a]-chinolizine$^1$)$^2$)" *Helv. Chim. Acta.* 41: 119–139, 1958.

(List continued on next page.)

*Primary Examiner*—Marianne M. Cintins
*Assistant Examiner*—Michael B. Hydorn
*Attorney, Agent, or Firm*—Woodcock Washburn Kurtz Mackiewicz & Norris

[57] ABSTRACT

Compounds of the formula

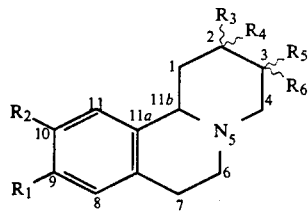

where
R$_1$ and R$_2$ are independently selected from the group consisting of H, OH, OCH$_3$, and Halogen or R$_1$ and R$_2$ can be taken together to form —O—CH$_2$—O—;
R$_3$ and R$_4$ are independently selected from the group consisting of H, OH, C$_1$-C$_{10}$ alkyl, C$_1$-C$_{10}$ alkoxy, C$_1$-C$_{10}$ alkenyloxy, —R$_7$—CH=CHI, and

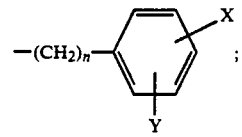

n is an integer from 0 to 5;
X and Y are independently selected from the group consisting of H, OH, OCH$_3$, Halogen and —R$_7$—CH=CHI;
R$_5$ and R$_6$ are independently selected from the group consisting of H, OH, C$_1$-C$_{10}$ alkyl, C$_1$-C$_{10}$ alkoxy, C$_1$-C$_{10}$ alkenyloxy, —R$_7$—CH=CHI, —CONR$_8$R$_9$ and

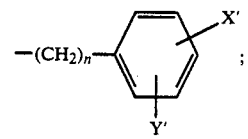

X' and Y' are independently selected from the group consisting of H, OH, OCH$_3$, Halogen, and —R$_7$—CH=CHI;
R$_7$ is selected from the group consisting of a chemical bond and C$_1$-C$_{10}$ alkyl; and
R$_8$ and R$_9$ are independently selected from the group consisting of H and C$_1$-C$_{10}$ alkyl;
provided that there is at least one iodine atom directly attached to a phenyl moiety or as part of a —CH=CHI moiety in one or more substituents selected from the group consisting of R$_3$, R$_4$, R$_5$ and R$_6$ are disclosed as being useful as imaging agents for evaluation of the central nervous system neuronal system.

20 Claims, 1 Drawing Sheet

OTHER PUBLICATIONS

Clarke, et al., "A Series of Hexahydro [1,4]oxazino[3,4-a]isoquinolines as Potential Neuroleptics." *J. Med. Chem.* 21: 785–791 (1978).

Cooper, et al., *Biochemical Basis of Neurochemistry*, 5th ed., Oxford University Press, New York: 290 (1986).

Darchen, et al., "Quantitative Autoradiography of the Rat Brain Vesicular Monamine Transporter Using the Binding of [$^3$H]Dihydrotetrabenazine and 7-Amino-8-[$^{125}$I]Iodoketanserin." Neurosci 33: 341–349 (1989).

Fahrenholtz, et al., "Octahydrophenanthrene Analogs of Tetrabenazine" *J. Med. Chem.* 9: 304–310 (1967).

Harnden, et al., "2-Thio-1,3,4,6,7,11b-hexahydro-9,10-dimethoxy-2H-benzo[a]quinolizines." *J. Med. Chem.* 10: 1183–1184 (1967).

Henry, et al., "Radioligands of the Vesicular Monoamine Transporter and Their Use as Markers of Monoamine Storage Vesicles (Commentary)" *Biochem Pharmacol* 38: 2395–2404 (1989).

Kaiser, et al., "Antipsychotic Agents", *Burger's Medicinal Chemistry* 4th Ed., ed. by Wolf M. E., Wiley Interscience, N.Y.: 859–964 (1981).

Lednicer, et al., *The Organic Chemistry of Drug Synthesis* Wiley-Interscience, Inc., N.Y.: 349–361 (1977).

Masuo, et al., "[$^3$H]Dihydrotetrabenazine, a new marker for the visualization of dopaminergic denervation in the rate striatum." *Neurosci Lett* 114: 45–50 (1990).

Meshgin-Azarian, et al., "Distribtution of [$^3$H]Dihydrotetrabenazine Binding in Bovine Striagal Subsynaptic Fracations: Enrichment of Higher Affinity Binding in a Synaptic Vesicle Fraction." *J. Neurochem.* 50: 824–830 (1988).

Near, J. A., "[$^3$H]Dihydrotetrabenazine Binding to Bovine Striatal Synaptic Vesicles" *Mol Pharmacol.* 30: 252–257 (1986).

Pletscher, et al., "Benzoquinolizine Derivatives: A New Class of Monoamine Decreasing Drugs with Psychotropic Action." *Rev. Neurobiol.* 4: 275–306 (1962).

Saner, et al., "A Benzo[a]Quinolizine Derivative with A Neuroleptic-Like Action on Cerebral Monoamine Turnover" *J. Pharmacol. Exp. Ther.* 203: 556–563 (1977).

Scherman et al., "[$^3$H]Dihydrotetrabenazine, a New In Vitro Monoaminergic Probe for Human Brain." *J. Neurochem.* 50: 1131–1136 (1988).

Scherman, et al., "Hydrophobicity of the Tetrabenzine-Binding Site of the Chromaffin Granule Monoamine Transporter". *Mol. Pharmacol* 33: 72–77 (1988).

Suchi, et al., "Covalent Modification of the Amine Transporter with N,N$^1$-Dicyclohexylcarbodiimide.+" *Biochem* 30: 6490–6494 (1991).

Darchen, et al., "Ketanserin Binds to the Monoamine Transporter of Chromaffin Granules and of Synaptic Vesicles", *Molecular Pharmacology* 33: 672–677 (1988).

Scherman, Daniel, "Dihydrotetrabenazine Binding and Monoamine Uptake in Mouse Brain Regions", *Journal of Neurochemistry*, vol. 47, No. 2: 331–339 (1986).

HPLC Separation of Isomers of I-TBZ

IODINE DERIVATIVES OF TETRABENAZINE

BACKGROUND OF THE INVENTION

This invention relates to a series of iodine derivatives of tetrabenazine (3-(2-methylpropyl)-9,10-dimethoxy-1,3,4,6,7,11b-hexahydro-2H-benzo[a]quinolizin-2-one, TBZ,1), a monoamine storage-site selective inhibitor, which iodine derivatives are useful as imaging agents for evaluation of the central nervous system (CNS) neuronal system.

Monoamine neuronal systems, i.e., serotonergic, dopaminergic and adrenergic neurotransmitters, have been implicated in various neurological and psychiatric disorders. Different types of therapeutic agents aiming at these neuronal systems, as the pharmacological basis for treatment, are well known. Evaluation of the innervation of these neuronal systems is essential and important for understanding the pathophysiology, and for monitoring progress of patient treatment. New and powerful imaging methods which enable one to assess the living brain in vivo and thereby monitor the effectiveness of drugs and substances that affect brain chemistry have recently been developed. Methods such as positron emission tomography (PET) and single photon emission tomography (SPECT) involve the administration to a patient of radioactive tracer substances comprising a ligand that binds to presynaptic or postsynaptic neuroreceptors in the patient's brain. Emissions (primarily gamma rays which are emitted from the positrons or photons emitted from the radioactive tracer) are measured. These emissions are indicative of the number and degree of occupancy or blocking of the neuroreceptors. The number of neuroreceptors and the degree of occupancy or blocking is calculated utilizing a mathematical model, and compared with an intra-person or inter-person control, to determine the degree of drug response. Further treatment of the patient with drugs can be based upon the comparisons made.

The CNS neuronal systems can take up selective neurotransmitters, such as dopamine, serotonin, norepinephrine etc, from either plasma or from the synaptic cleft. This reuptake process is achieved by a selective transport mechanism based on a specific reuptake receptor on the specific type of presynaptic neuronal terminal. However, once the transmitters are inside the specific type of neuron, a second transporter or reuptake and storage mechanism is responsible for storing and packing the neurotransmitters in vesicles (or granules).

The second transport mechanism, contrary to that for the presynaptic reuptake, is based on a common ATP-dependent transporter which resides on the surface of the vesicles. The second transporters are non-selective and are effective for catecholamines, serotonin and histamine. The neurotransmitters stored in the vesicles are protected from degradation by monoamine oxidases (MAOs) in the cytosol. When neural transmissions are induced by electrical signals, the vesicles in the presynaptic neurons are fused with the membrane and the stored neurotransmitters are released into the synaptic cleft for postsynaptic receptor binding, which leads to further signal transduction.

Reserpine is a natural product which inhibits the monoamine uptake-storage mechanism of amine granules in the synapse. Tetrabenazine, 3-(2-methylpropyl)-9,10-dimethoxy-1,3,4,6,7,11b-hexahydro-2H-benzo[a]quinolizin-2-one (TBZ),

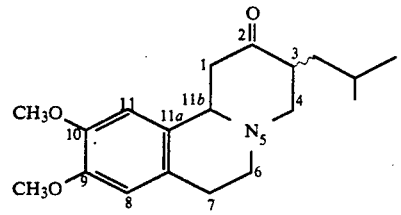

is an analog of reserpine which displays a similar biological profile. Due to their ability to deplete monoamines in the CNS, both were used as antipsychotic agents in the 1950's (Cooper J. R., Bloom F. E., Ruth R. H., In *Biochemical Basis of Neurochemistry*, 5th ed., Oxford University Press, New York, 1986, p. 290; Neumeyer J. L., Neuroleptics and axiolytic agents. In *Principles of Medicinal Chemistry*, Foye, W. O., ed. Lea and Febiger, Philadelphia, Pa., 1981; Kaiser C., Setler P. E., Antipsychotic agents. *Burger's Medicinal Chemistry*, 4th Ed. Wolf M. E., ed. Wiley-Interscience, New York, 1981, pp 860–964). The depletion of catecholamines and serotonin in the brain by reserpine is long-lasting and the storage mechanism is irreversibly damaged. Tetrabenazine produces a similar effect; however, the drug effects of TBZ are of a shorter duration and do not cause irreversible damage to neurons (Cooper J. R., Bloom F. E., Ruth R. H., In *Biochemical Basis of Neurochemistry*, 5th ed., Oxford University Press, New York, 1986, p. 290; Neumeyer J. L., Neuroleptics and axiolytic agents. In *Principles of Medicinal Chemistry*, Foye, W. O., ed. Lea and Febiger, Philadelphia, Pa., 1981). Clinical studies appear to suggest that treatment of patients with TBZ with up to 300 mg daily improved tardive dyskinesia in several trials (Neumeyer J. L., Neuroleptics and axiolytic agents. In *Principles of Medicinal Chemistry*, Foye, W. O., ed. Lea and Febiger, Philadelphia, Pa., 1981).

Recently, [$^3$H]dihydro-TBZ (2-hydroxy-3-(2-methylpropyl)-9,10-dimethoxy-1,3,4,6,7,11b-hexahydro-2H-benzo[a]quinolizine) has been used as a selective marker for the monoamine transport system in vitro. A detailed review of the use of [$^3$H]dihydro-TBZ and [$^3$H]reserpine as ligands for in vitro investigation of the monoamine transporter of chromaffin granules and CNS synaptic vesicles was published recently (Henry, J. P., Scherman D., Radioligands of the vesicular monoamine transporter and their use as markers of monoamine storage vesicles (Commentary). Biochem Pharmacol 38:2395–2404, 1989). In vitro binding studies of [$^3$H]dihydro-TBZ using membranes of chromaffin granules and brain tissue samples demonstrated a high binding affinity (Kd=2–9 nM) (Darchen F., Masuo Y., Vial M., Rostene W., Scherman D., Quantitative autoradiography of the rat brain vesicular monoamine transporter using the binding of [$^3$H]dihydrotetrabenazine and 7-amino-8-[$^{125}$I]iodoketanserin. Neurosci 33:341–349, 1989; Meshgin-Azarian S., Chang W., Cugier D. L., Vincent M. S., Near J. A., Distribution of [$^3$H]dihydrotetrabenazine binding in bovine striatal subsynaptic fractions: Enrichment of higher affinity binding in a synaptic vesicle fraction. J. Neurochem 50:824–830, 1988; Near J. A., [$^3$H]Dihydrotetrabenazine binding to bovine striatal subsynaptic vesicles. Mol Pharmacol 30:252–257, 1986; Scherman D., Raisman R., Ploska A., Agid Y., [³H]Dihydrotetrabenazine, a new in vitro monoaminergic probe for human brain. J. Neurochem 50:1131-1136, 1988; Suchi R., Stern-Bach Y., Gabay T., Schuldiner S. Covalent modification of the amine transporter with N,N'-dicyclohexylcarbodiimide. Biochem 30:6490-6494, 1991).

The regional distribution of the dihydro-TBZ binding sites in brain sections corresponded to the monoamine cell bodies and nerve endings in normal and lesioned brain sections (Masuo Y., Pelaprat D., Scherman D., Rostene W., [³H]Dihydro-tetrabenazine, a new marker for the visualization of dopaminergic denervation in the rat stratum. Neurosci Lett 114:45-50, 1990). Various derivatives of TBZ have been reported (Kaiser C., Setler P. E., Antipsychotic agents. *Burger's Medicinal Chemistry*, 4th Ed. Wolf ME, ed. Wiley-Interscience, New York, 1981, pp 860-964; Neumeyer J. L., Neuroleptics and axiolytic agents. In *Principles of Medicinal Chemistry*, Foye, W. O. ed. Lea and Febiger, Philadelphia, Pa., 1981; Clarke F. H., Hill R. T., Koo J., Lopano R. M., Maseda M. A., Smith M., Soled S., VonVeh G., Vlattas I. A series of hexahydro[1,4]oxazino[3,4-a]isoquinolines as potential neuroleptics. J. Med. Chem. 21:785-791, 1978; Saner A., Pletscher A. A benzo[a]-quinoline derivative with a neuroleptic-like action on cerebral monoamine turnover. J. Pharmacol. Exp. Ther. 203:556-563, 1977; Lednicer D., Mitscher L. A. *The Organic Chemistry of Drug Synthesis*. Wiley-Interscience Inc., New York, 1977, pp 349-361; Fahrenholtz K. E., Capomaggi A., Lurie M., Goldberg M. W., Kierstead R. W. Octahydrophenanthrene analogs of tetrabenazine J. Med. Chem. 9:304-310, 1967; Harnden M. R., Short J. H. 2-Thiol-1,3,4,6,7,11b-hexahydro-9,10-dimethoxy-2H-benzo[a]quinolizines. J. Med. Chem. 10:1183-1184, 1967; Tretter J. R., U.S. Pat. No. 3,053,845, 1962; Pletscher A., Brossi A., Gey K. F. Benzoquinoline derivatives: A new class of monoamine decreasing drugs with psychotropic action. Rev. Neurobiol. 4:275-302, 1962; Brossi A., Lidlar H., Walter M., Schnider O. 16. Synthesenversuche in der Emetin-Reihe. 1. Mitteilung. 2-Oxo-hydrobenz[a]chiolizine. Helv. Chim. Acta. 41:119-139, 1958). Reduction of the ketone to dihydro-TBZ does not affect the binding affinity. The alkylated alcohol derivatives also displayed high potency. In addition, the acetyl derivative of dihydro-TBZ has also been shown to retain high affinity for the transporter. (Scherman D., Gasnier B., Jaudon P., Henry J. P. Hydrophobicity of the tetrabenazine-binding site of the chromaffin granule monoamine transporter. Mol. Pharmacol. 33:72-77, 1988).

The determination of neuronal integrity can be important in differential diagnosis of CNS diseases. An imaging agent for PET and SPECT, which could be useful for evaluation of the presynaptic neuronal functions, especially the uptake and storage mechanism, could serve the need of a large population of patients receiving drug treatments targeting the monoamine neurons.

SUMMARY OF THE INVENTION

Tests indicate that novel iodine TBZ derivatives of Formula I can cross the intact blood brain barrier and localize in the brain and should therefore be useful as imaging agents for studying CNS monoamine uptake sites.

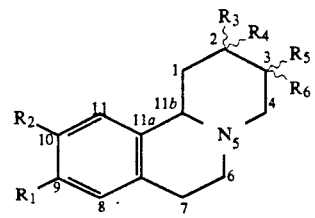

Formula I where $R_1$ and $R_2$ are independently selected from the group consisting of H, OH, $OCH_3$, and Halogen or $R_1$ and $R_2$ can be taken together to form $-O-CH_2-O-$;

$R_3$ and $R_4$ are independently selected from the group consisting of H, OH, $C_1-C_{10}$ alkyl, $C_1-C_{10}$ alkoxy, $C_1-C_{10}$ alkenyloxy, $-R_7-CH=CHI$, and

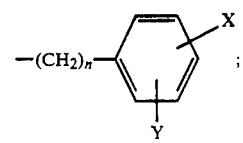

n is an integer from 0 to 5;

X and Y are independently selected from the group consisting of H, OH, $OCH_3$, Halogen and $-R_7-CH=CHI$;

$R_5$ and $R_6$ are independently selected from the group consisting of H, OH, $C_1-C_{10}$ alkyl, $C_1-C_{10}$ alkoxy, $C_1-C_{10}$ alkenyloxy, $-R_7-CH=CHI$, $-CONR_8R_9$ and

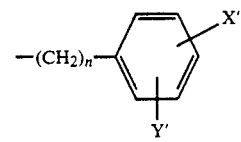

X' and Y' are independently selected from the group consisting of H, OH, $OCH_3$, Halogen, and $-R_7-CH=CHI$;

$R_7$ is selected from the group consisting of a chemical bond and $C_1-C_{10}$ alkyl; and $R_8$ and $R_9$ are independently selected from the group consisting of H, and $C_1-C_{10}$ alkyl;

provided that there is at least one iodine atom directly attached to a phenyl moiety or as part of a $-CH=CHI$ moiety.

This invention therefore relates to the compounds of Formula I and to methods of utilizing them as imaging agents for the evaluation of patients having or suspected of having neurological and psychiatric disorders. Tests indicate that these compounds should not be specific for one type of neuronal systems, but will be useful as a general indicator for combined neuronal activity of serotonergic, dopaminergic and adrenergic systems.

DETAILED DESCRIPTION OF THE INVENTION

Figure 1:
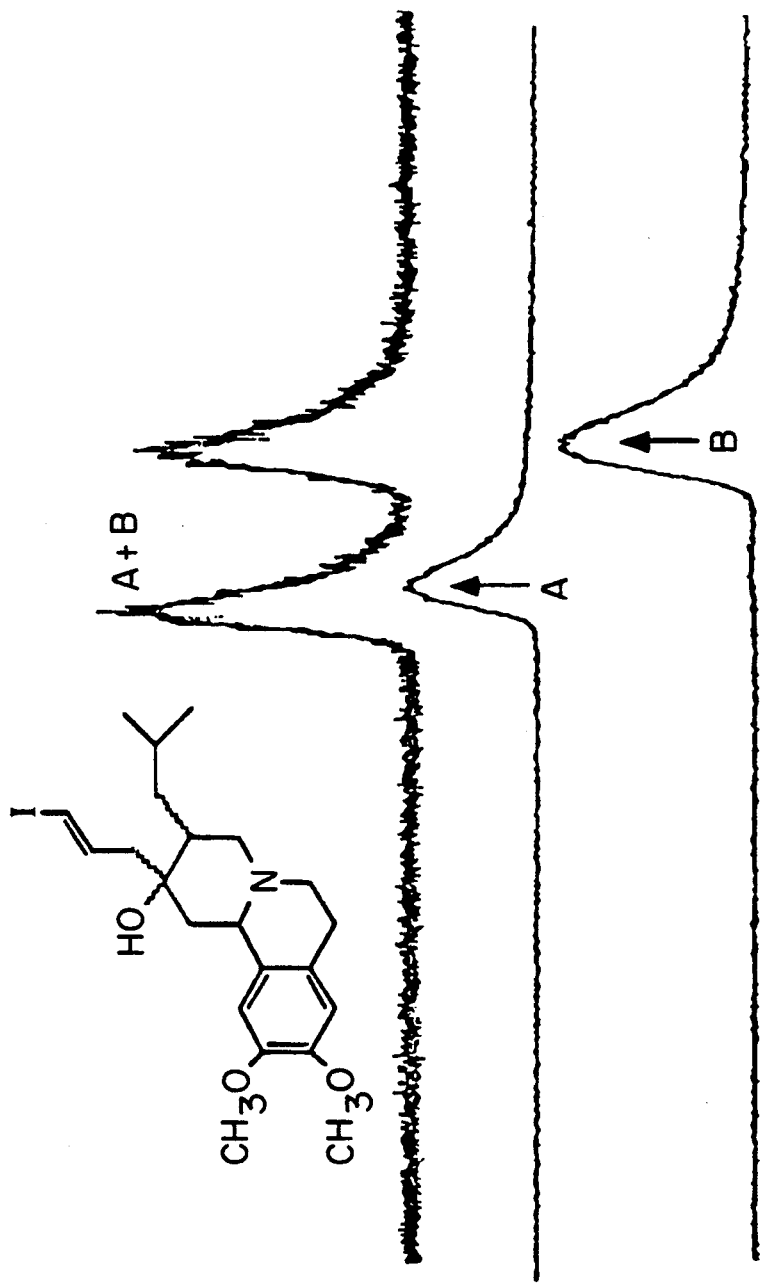
FIG. 1 is the HPLC profile of a racemic mixture of, and resolved isomers of, the compound 2-hydroxy-2-iodovinyl-3-(2-methylpropyl)-9,10-dimethoxy-1,3,4,6,7,11b -hexahydro-2H-benzo[a]quinolizine (I-TBZ).

As used herein, the term "halogen" encompasses atoms of fluorine, chlorine, bromine and iodine. The term "alkyl" encompasses straight-chained, branched and cyclic alkyl groups. Alkoxy groups are groups of the formula —O—alkyl, and alkenyloxy groups are groups of the formula —O—alkene.

The term "radioactive iodine isotope" encompasses the isotopes $^{121}$I, $^{123}$I and $^{125}$I. Although $^{125}$I-isotopes are useful for laboratory testing, they will generally not be useful for actual diagnostic purposes because of the relatively long half-life (60 days) and low gamma-emission (30–65 Kev) of $^{125}$I. The isotope $^{123}$I has a half life of 13 hours, gamma energy 159 keV), and it is therefore expected that labeling of ligands to be used for diagnostic purposes would be with this isotope. The isotope $^{121}$I, with a half life of 2 hours, may also be useful for diagnostic purposes.

Preferred compounds of this invention are those compounds of Formula I where, independently, (a) $R_3$ and $R_4$ are independently selected from the group consisting of H, —$R_7$—CH=CHI, OH, and OCH$_3$, and (b) $R_5$ and $R_6$ are independently selected from the group consisting of H, $C_1$–$C_4$ alkyl, and —CONR$_8$R$_9$ where $R_8$ and $R_9$ are independently selected from the group consisting of H and $C_1$–$C_4$ alkyl. More preferred are those compounds of this invention where, independently, (a) one of $R_3$ and $R_4$ is —CH=CHI and (b) one of $R_5$ and $R_6$ is selected from the group consisting of —CON($C_2H_5$)$_2$ and methylpropyl. A specifically preferred compound is 2-hydroxy-2-iodovinyl-3-(2-methylpropyl)-9,10-dimethoxy-1,3,4,6,7,11b-hexahydro-2H-benzo[a]quinolizine (iodovinyl-TBZ).

Examples of compounds included within the scope of this invention are provided in Table 1

TABLE 1

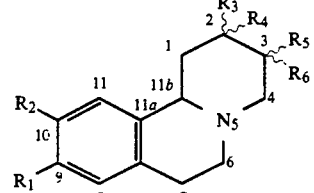

| $R_1$ | $R_2$ | $R_3$ | $R_4$ | $R_5$ | $R_6$ |
|---|---|---|---|---|---|
| OCH$_3$ | OCH$_3$ | OH | CH=CHI | I | CH$_2$CH(CH$_3$)$_2$ |
| —O—CH$_2$—O— | | OH | CH=CHI | H | CH$_2$CH(CH$_3$)$_2$ |
| OCH$_3$ | OCH$_3$ | OH | H | H | CH$_2$CH=CHI |
| Cl | OCH$_3$ | OH | CH=CHI | H | CH$_2$CH(CH$_3$)$_2$ |
| I | OCH$_3$ | OH | H | H | CH$_2$CH(CH$_3$)$_2$ |
| Cl | OH | OH | CH=CHI | H | CH$_2$CH(CH$_3$)$_2$ |
| OH | OCH$_3$ | OCH$_3$ | CH=CHI | H | CH$_2$CH(CH$_3$)$_2$ |
| I | OH | OH | H | H | CH$_2$CH(CH$_3$)$_2$ |
| OCH$_3$ | OCH$_3$ | OH | CH=CHI | H | C(O)N(C$_2$H$_5$)$_2$ |
| —O—CH$_2$—O— | | OH | CH=CHI | H | C(O)N(C$_2$H$_5$)$_2$ |
| Cl | OCH$_3$ | OH | CH=CHI | H | C(O)N(C$_2$H$_5$)$_2$ |
| I | OCH$_3$ | OH | H | H | C(O)N(C$_2$H$_5$)$_2$ |
| Cl | OH | OH | CH=CHI | H | C(O)N(C$_2$H$_5$)$_2$ |
| OH | OCH$_3$ | OCH$_3$ | CH=CHI | H | C(O)N(C$_2$H$_5$)$_2$ |
| I | OH | OH | H | H | C(O)N(C$_2$H$_5$)$_2$ |

Compounds of this invention may be prepared by methods analogous to that shown below in Scheme I for the preparation of iodovinyl-TBZ. Ethynylation of tetrabenazine (TBZ, 1) may be accomplished by first treating trimethylsilylacetylene with n-butyllithium at −5° to 0° C. in tetrahydrofuran (THF), followed by dropwise addition of a solution of TBZ in THF. The trimethylsilyl group can be removed using 5N NaOH. The ethynyl derivative (3) can then be treated with tri-n-butyltin hydride in the presence of azobisisobutyronitrile (AIBN) and heating the mixture to 95° C. for 5 hours. Treatment of the vinylstannane (4) intermediate dissolved in CHCl$_3$ with a 0.1M solution of iodine in CHCl$_3$ affords the cold iodinated compound (2a) in 27.5% overall yield.

Scheme I

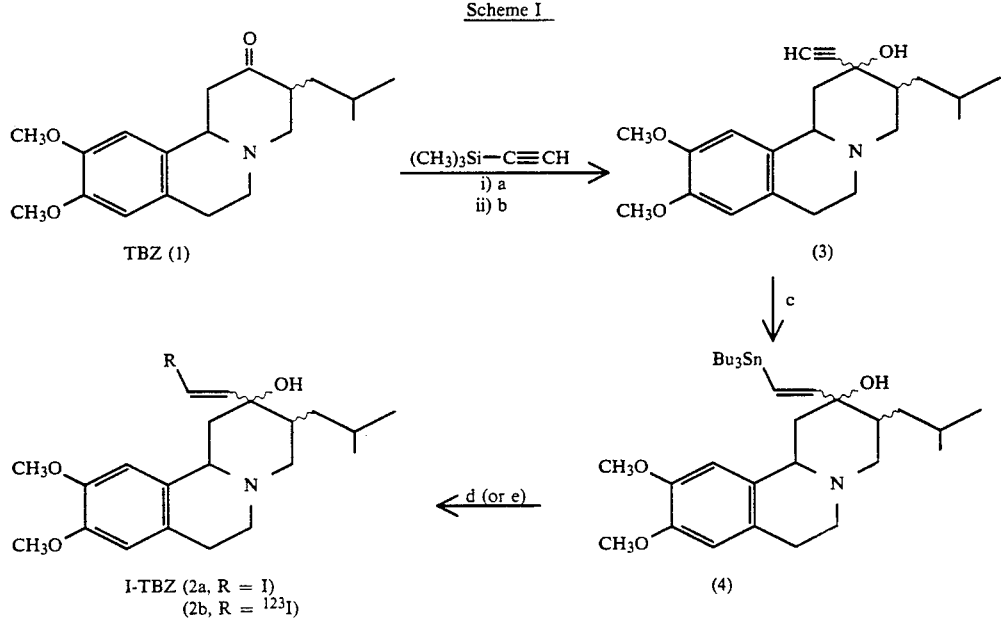

a) n-butyl Li, THF, 0° C.;
b) KOH, MeOH, 65° C.;

-continued
Scheme I c) HSnBu$_3$, AIBN, Toluene, 95° C.;
d) I$_2$, CHCL$_3$, 25° C.;
e) Na$^{123}$I, 1N HCl/EtOH, H$_2$O$_2$ The radiolabeled derivative (2b) can be prepared by treating an ethanolic solution of the organotin intermediate with Na$^{123}$I and 1N HCl in the presence of H$_2$O$_2$. After an HPLC purification, the radiochemically pure compound displayed the same retention time as that of the authentic cold compound. To further characterize the proposed agent, optical isomer separation of no-carrier-added [$^{123}$I]-2b in conjunction with a chiralcel OD column (eluted with n-hexane/ethanol 95/5, 1 ml/min) was carried out FIG. 1 presents the HPLC profiles of the racemic mixture and the resolved isomers, suggesting that at least two isomers (out of a theoretical possibility of eight) can be separated.

Additional starting materials for use analogously in the method shown in Scheme I, to prepare additional compounds of this invention, may be prepared as illustrated below in Schemes II, III and IV. Scheme V illustrates the preparation of a key intermediates, from commercially available phenethylamines, which key intermediates may be used as starting materials in Schemes I-IV. One skilled in the art will recognize that key intermediates other than those expressly shown in Scheme V may be made by analogous methods. Variations of the illustrated syntheses, to produce other compounds of the invention, would be known to one skilled in the art. Scheme II Scheme II

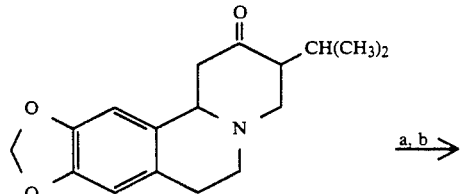

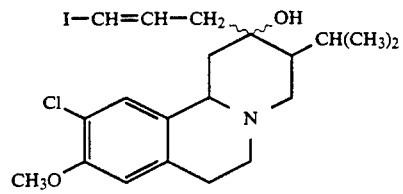

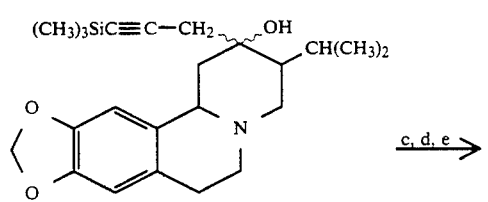

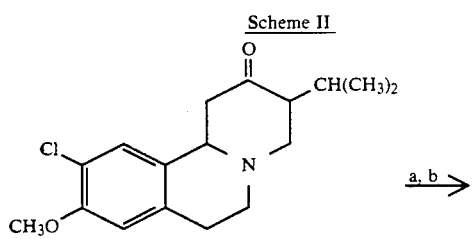

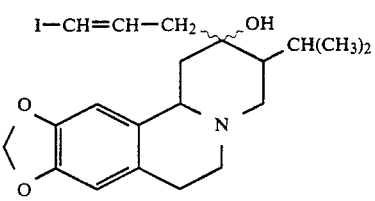

a. n-BuLi;
b. (CH$_3$)$_3$SiC≡CH;
c. KOH;
d. HSn(n-Bu)$_3$;
e. I$_2$.

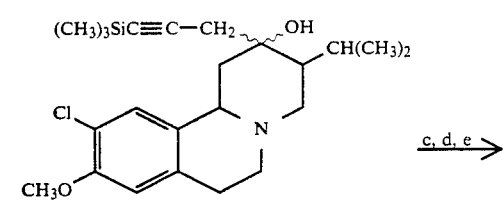

Scheme III

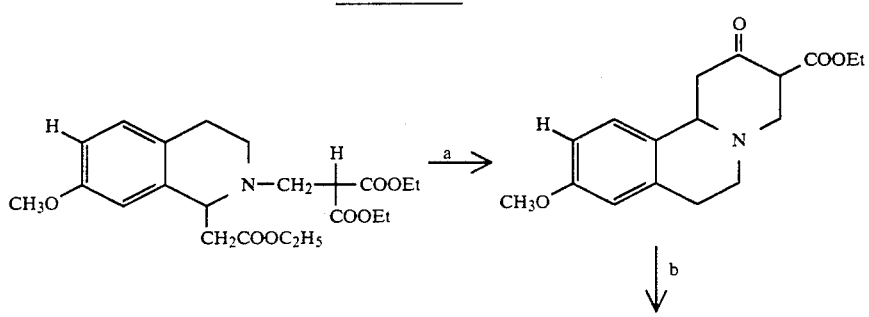

-continued
Scheme III
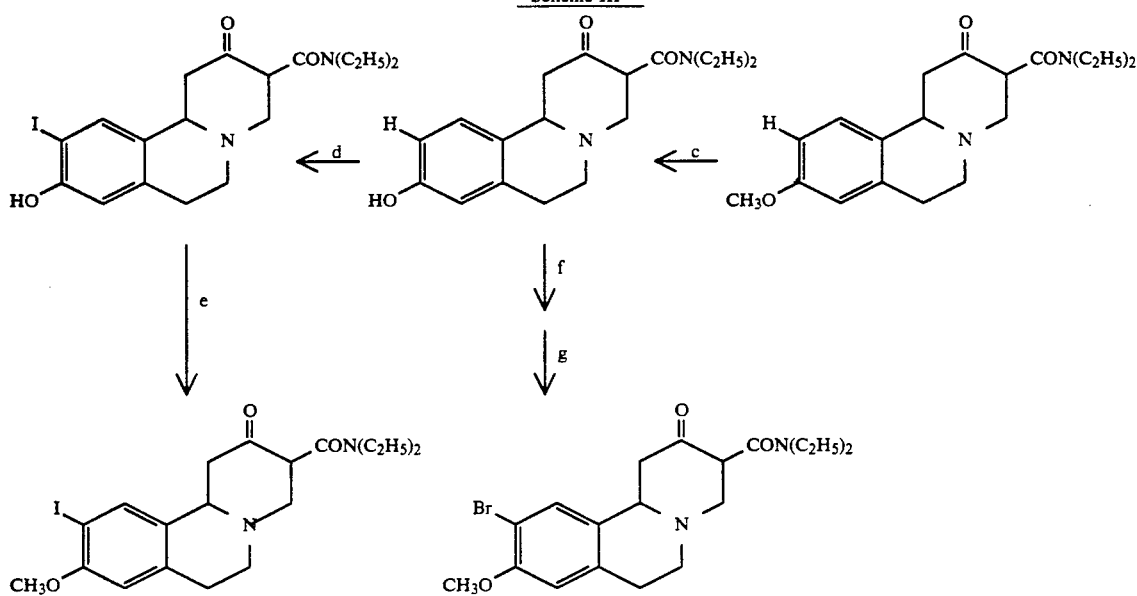
a. condensation (acid, heat);
b. KOH; SOCl; (C₂H₅)₂NH;
c. BBr₃;
d. I₂;
e. CH₃I;
f. Br₂;
g. CH₃I.
Scheme IV
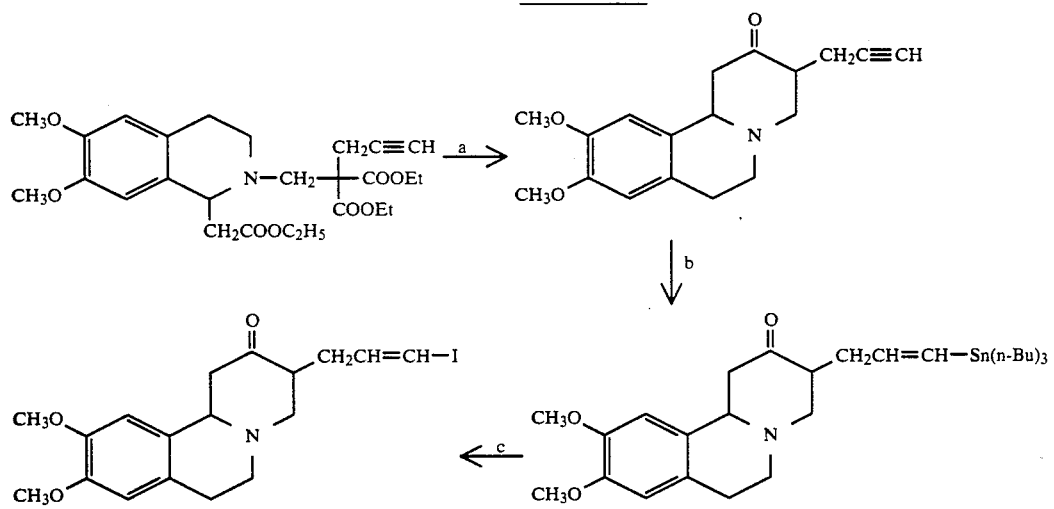
a. condensation (acid, heat);
b. HSn(n-Bu)₃;
c. I₂.
Scheme V
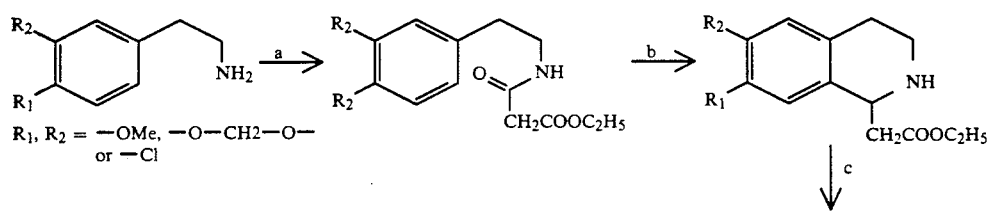
$R_1, R_2$ = —OMe, —O—CH₂—O—
or —Cl

Scheme V -continued

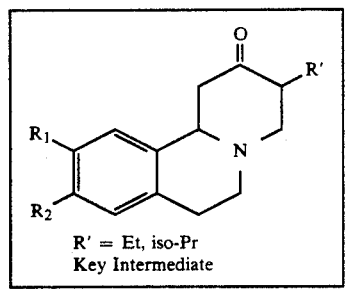 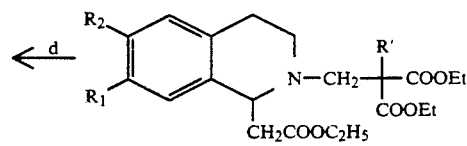

R' = Et, iso-Pr
Key Intermediate a. coupling with malonyl chloride;
b. dehydration, condensation;
c. alkylation;
d. condensation (acid, heat).

Biodistribution of [$^{123}$I]-2b (see Scheme I) in rats showed that the TBZ derivative can cross the intact blood brain barrier and localize in the brain. However, the regional distribution ratio in the rat brain did not exhibit any selectivity. The lack of regional difference reflecting the distribution of monoamine neurons may be due to the fact that there are three optical centers for 2a.

Compounds of this invention containing a radioactive iodine isotope may be used in methods such as positron emission tomography and single photon emission tomography to image CNS monoamine uptake sites in the brain. The compounds may be administered, usually in formulations with pharmaceutically acceptable carriers or diluents known in the art, by any means which will effectively administer them to the brain of a patient. Typically, such administration is parenteral or intravenous.

The following examples are provided to further illustrate the preparation and activity of the compounds of this invention and are not intended to be limiting thereof.

Reagents used in syntheses were purchased from Aldrich Chemical Co. (Milwaukee, Wis.) and used without further purification unless otherwise indicated. Tetrabenazine was purchased from Fluka. Anhydrous sodium sulfate (Na$_2$SO$_4$) was used as a drying agent. Reaction yields were reported without further optimization. Reagent-grade and HPLC-grade solvents were obtained from Emsco Co. (Philadelphia, Pa.). Tetrahydrofuran was dried by distillation from sodium benzophenone ketyl. Toluene was dried by distillation from sodium metal. Thin layer chromatography (TLC) was performed on EM Science (Gibbstown, N.J.) precoated (0.2 mm) silica gel 60 plates and the spots were detected with I$_2$ vapor and/or UV light. Silica gel 60 (70-230 mesh) obtained from EM Science (Gibbstown, N.J.) was used for column chromatography. $^1$H and $^{13}$C spectra were obtained on a Bruker Model AM 500 or a Varian 360A spectrometer. Unless otherwise specified, all samples were run in CDCl$_3$ purchased from Aldrich Chemical Co. Chemical shifts are reported as δ values with the chloroform or tetramethylsilane resonance used as the internal standard. The multiplicity is defined by s (singlet), d (doublet), t (triplet), q (quarter), and m (multiplet). The relative peak heights of the resonances are reported as integers after the multiplicity. IR spectra were recorded (KBr pellet or neat as a film) with a Mattson Polaris FT-IR spectrometer. Melting points were determined on a Meltemp apparatus (Cambridge, Mass.) and are reported uncorrected. Elemental analyses were performed by Atlantic Microlabs Inc. (Norcross, Ga.). Optical rotation was measured with a polarimeter model 243B by Perkin-Elmer. A Rainin liquid chromatograph equipped with a PRP-1 reverse phase cartridge (Hamilton) or a chiral column (Chiralcel, Daicel Chemical Industries, Ltd.) was used for high-performance liquid chromatographic (HPLC) separations and analyses. Reaction yields were reported without further optimization.

EXAMPLE 1

2-Hydroxy-2-ethynyl-3-(2-methylpropyl)-9,10-dimethoxy -1,3,4,6,7,11b-hexahydro-2H-benzo[a]quinolizine (3).

Trimethylsilylacetylene (2 eqs.; 20.4 mmol; 2.88 mL) was dissolved in 80 mL of dry THF and stirred under a nitrogen atmosphere at −5° to 0° C. n-Butyl lithium (20.4 mmol, 12.72 mL) was added dropwise with stirring followed by dropwise addition of a solution of 3-isobutyl-9-,10-dimethoxy-1,3,4,6,7,11b-hexahydro-2H-benzo[a]quinolizin-2-one (TBZ) in 30 mL dry THF. The reaction mixture was stirred at −5° to 0° C. for 1 h, allowed to warm slowly to 20° C., and stirred for 2 h at 20° C. The reaction was quenched while cold with saturated NH$_4$Cl. The solvent was evaporated under reduced pressure and the resulting aqueous solution was extracted with ethyl acetate (3×100 mL). The organic phase was washed with water (2×50 mL) and brine (50 mL) and concentrated. The residue was dissolved in 30 mL MeOH and 5 mL 5N KOH, and heated to 65° C. with stirring for 30 min. The reaction was cooled and quenched with NH$_4$Cl. The methanol was evaporated and the aqueous phase extracted with ethyl acetate (3×75 mL). The organic phase was washed with water (50 mL) and brine (50 mL), dried over Na$_2$SO$_4$, and concentrated to yield the product (53.7%) as slightly brown solid.

Compound 3:

|   | Calculated | Found |
|---|---|---|
| C | 73.44 | 73.50 |
| H | 8.51 | 8.48 |
| N | 4.08 | 4.09 |

EXAMPLE 2

2-(2-Tri-n-butylstannylethenyl)-2-hydroxy-3-(2-methylpropyl)-9,10-dimethoxy-1,3,4,6,7,11b-hexahydro-2H-benzo[a]quinolizine (4).

The alkyne, 2-hydroxy-2-ethynyl-3-(2-methylpropyl)-9,10-dimethoxy-1,3,4,6,7,11b -hexahydrobenzo[a]quinolizine (3), was dissolved in 50 mL dry toluene and treated with tri-n-butyltin hydride (2 eqs. 9.7 mmol; 2.6 mL) while stirring under an argon atmosphere. Azobisisobutyronitrile (AIBN) was added (30 mg) and the mixture was heated to 95° C. for 5 h. The reaction mixture was cooled and the solvent evaporated under reduced pressure. The residue was chromatographed on a silica gel column and eluted with ethyl acetate/hexane (1:1) to afford 1.89 g (60.8%) of 3 as an oil. A second column chromatography was performed to obtain an analytically pure sample.

Compound 4:

|   | Calculated | Found |
|---|---|---|
| C | 62.47 | 62.42 |
| H | 9.05 | 9.10 |
| N | 2.21 | 2.26 |

EXAMPLE 3

2-Hydroxy-2-iodovinyl-3-(2-methylpropyl) -9,10-dimethoxy-1,2,3,4,6,7,11b-hexahydro-2H -benzo[a]quinolizine (2).

The vinylstannane intermediate (0.24 g; 0.38 mmol) was dissolved in 15 mL CHCl$_3$ and stirred at room temperature. A 0.1M solution of I$_2$ in CHCl$_3$ was added dropwise until a brown color persisted. The reaction was stirred at r.t. for 24 h and then quenched with 2 mL of a 1M solution of KF in methanol and 2 mL 5% aqueous sodium bisulfite. The layers were separated and the aqueous layer extracted with CHCl$_3$ (3×20 mL). Organic layers were combined, washed with water (2×20 ml) and brine (20 mL), dried over anhydrous sodium sulfate and concentrated to yield (84.3%) 2 as a slightly yellow oil.

Compound 2:

|   | Calculated | Found |
|---|---|---|
| C | 53.51 | 53.27 |
| H | 6.41 | 6.56 |
| N | 2.97 | 2.81 |

EXAMPLE 4

Radiolabeling

The I-23 labeled iodovinYl-TBZ derivative ([$^{123}$I]-TBZ, 2b) was prepared by an iododestannylation reaction. Aqueous hydrogen peroxide (1 mg/mL EtOH), 200 uL of 0.1 N HCl and 5 mCi [$^{123}$I]sodium iodide were combined in a sealed vial. The reaction was allowed to proceed at room temperature for 20 min, after which it was terminated by addition of 0.1 mL sodium bisulfite (300 mg/ml). The reaction was then neutralized with NaHCO$_3$ and extracted with ethyl acetate (3×1 mL). The combined organic layers were dried under nitrogen and the desired product was purified through HPLC on a reverse phase column (PRP-1, Hamilton) eluting with a isocratic solvent of 90% acetonitrile-10% buffer (5 mM 3,3'-dimethylglutaric acid, pH 7.0) and a flow rate of 1 mL/min. The radiochemical purity was analyzed by the above chromatographic system and the purified [$^{123}$I] product (yield 50%, purity >98%) was obtained for animal experiments. The radiolabeled [$^{123}$I]I-TBZ is stable at room temperature for up to 15 h.

EXAMPLE 5

Separation of Isomers

Separation of optical isomers was achieved by HPLC in conjunction with a chiral column (Chiracel OD, Diacel, Irving, Calif.). Samples were injected and eluted with hexane/ethanol 95/5, 1 mL/min and the fractions of peaks A and B (FIG. 1) were collected. The combined fractions for each isomer were condensed and re-extracted with ethyl acetate. The ethyl acetate solution of each fraction was condensed redissolved in ethanol. Small samples of each of the purified optical isomers were reinjected and checked for optical purity using the same HPLC system. Peaks A and B showed an optical purity of 99% and 97%; retention times were 11.0 and 13.6 min, respectively.

EXAMPLE 6

Protein binding

One ml of 10% rat plasma was mixed with [$^{123}$I]I-TBZ in a test tube and the mixture was incubated for 30 minutes at 37° C. To the mixture 0.4 mL of 10% trichloroacetic acid (TCA) was added. The test tube was centrifuged for 10 min. (4,000 rpm), and the top aqueous layer was removed to another test tube for counting The precipitate was washed with water (0.5 mL×2). The combined water and top aqueous layer was counted. The residual precipitate was also counted. The protein binding was obtained by dividing counts in precipitate with counts in aqueous layers.

One mL of rat plasma (50%) was mixed with [$^{123}$I]I-TBZ in a test tube. After 30 min incubation at 37° C., 50 uL ×3 of liquid was removed as initial dose standard (I.D.); the rest was passed through an Amicon micropartition system (Amicon division, W. R. Grace, Danvers, Mass.) by centrifuging for 20 minutes (2,000 rpm) at 0° C. Four samples (50 uL each) were removed from the filtered solution and counted. The protein binding (% bound) was calculated by using the unit counts in filtrate divided by unit counts in ID.

Results are presented in Table 2.

TABLE 2

| PROTEIN BINDING TEST (% BOUND) | | |
|---|---|---|
|  | by TCA | by Filter |
| Peak-A | 38.1 ± 1.5 | 81.8 ± 0.5 |
| Peak-B | 40.8 ± 0.6 | 83.7 ± 0.8 |

EXAMPLE 7

Biodistribution in rats

While under ether anesthesia, each rat was injected in the femoral vein with 0.2 mL saline solution containing [$^{123}$I]I-TBZ (1-5uCi) either racemic mixture, peak-A or peak-B. The rats were sacrificed at various time points postinjection by cardiac excision. The tissues were weighed and the radioactivity was measured with a Canberra gamma counter (Model 5000). The percent dose per organ was calculated by a comparison of the tissue counts to suitably diluted aliquots of the injected material. Total activities of blood and muscle were calculated assuming that they were 7% and 40% of total body weight, respectively Results are presented in Tables 3, 4A and 4B.

TABLE 3

Biodistribution of [$^{123}$I]I-TBZ racemic mixture in rats (iv injection)
(% Dose/organ, Average of 3 rats ± S)

| Organ | 2 min | 30 min | 60 min | 120 min | 240 min | 6 hr* | 16 hr |
|---|---|---|---|---|---|---|---|
| Blood | 5.99 ± 2.54 | 1.84 ± 0.17 | 2.46 ± 0.56 | 2.16 ± 0.21 | 1.82 ± 0.26 | 1.58 ± 0.15 | 0.42 ± 0.07 |
| Heart | 1.33 ± 0.19 | 0.34 ± 0.02 | 0.35 ± 0.06 | 0.24 ± 0.06 | 0.18 ± 0.03 | 0.11 ± 0.01 | 0.02 ± 0.003 |
| Muscle | 6.93 ± 0.12 | 20.18 ± 2.19 | 14.9 ± 1.77 | 15.4 ± 4.17 | 11.24 ± 2.57 | 6.94 ± 0.93 | 1.49 ± 0.23 |
| Lung | 4.44 ± 1.44 | 1.02 ± 0.14 | 1.47 ± 0.64 | 0.78 ± 0.43 | 0.54 ± 0.09 | 0.36 | 0.07 ± 0.006 |
| Kidney | 4.18 ± 0.46 | 1.55 ± 0.21 | 1.47 ± 0.22 | 0.97 ± 0.13 | 0.73 ± 0.13 | 0.45 ± 0.03 | 0.12 ± 0.015 |
| Spleen | 0.28 ± 0.04 | 0.29 ± 0.03 | 0.37 ± 0.10 | 0.20 ± 0.06 | 0.18 ± 0.02 | 0.11 ± 0.004 | 0.02 ± 0.002 |
| Liver | 11.1 ± 1.22 | 9.75 ± 1.83 | 8.57 ± 0.41 | 6.71 ± 0.84 | 4.57 ± 0.69 | 3.21 ± 0.28 | 1.32 ± 0.096 |
| Skin | 4.08 ± 2.32 | 11.53 ± 2.54 | 6.39 ± 2.37 | 7.05 ± 1.52 | 4.21 ± 0.25 | 4.15 ± 0.63 | 2.04 ± 0.18 |
| Thyroid | 0.06 ± 0.02 | 0.03 ± 0.005 | 0.05 ± 0.002 | 0.08 ± 0.05 | 0.15 ± 0.18 | 0.42 ± 0.15 | 0.009 ± 0.004 |
| Brain | 0.92 ± 0.13 | 0.36 ± 0.05 | 0.28 ± 0.05 | 0.16 ± 0.03 | 0.13 ± 0.04 | 0.05 ± 0.001 | 0.008 ± 0.001 |
| | | | Regional brain uptake (% Dose/g, ratio) | | | | |
| CB | 0.50 ± 0.13 | 0.17 ± 0.03 | 0.14 ± 0.04 | 0.14 ± 0.003 | 0.051 ± 0.014 | 0.025 ± 0.0002 | 0.0063 ± 0.0010 |
| ST | 0.54 ± 0.21 | 0.21 ± 0.006 | 0.15 ± 0.03 | 0.12 ± 0.04 | 0.056 ± 0.014 | 0.024 ± 0.0029 | 0.0062 ± 0.0026 |
| HP | 0.58 ± 0.16 | 0.21 ± 0.020 | 0.14 ± 0.02 | 0.12 ± 0.04 | 0.048 ± 0.015 | 0.028 ± 0.0064 | 0.0051 ± 0.0020 |
| CX | 0.55 ± 0.24 | 0.20 ± 0.02 | 0.14 ± 0.04 | 0.15 ± 0.09 | 0.052 ± 0.021 | 0.022 | 0.0061 ± 0.0013 |

CB: cerebellum; ST: striatum; HP: hippocampus; CX: cortex
*2 rats only

TABLE 4A

Biodistribution of [$^{123}$I]I-TBZ in rats (iv injection)
(% Dose/organ, Average of 3 rats ± SD)
Peak A

| Organ | Time (min.) post-injection | | | | |
|---|---|---|---|---|---|
| | 5 | 20 | 60 | 120 | 20* |
| Blood | 2.15 ± 0.11 | 1.42 ± 0.56 | 1.14 ± 0.16 | 0.95 ± 0.03 | 2.05 ± 0.21 |
| Heart | 0.91 ± 0.17 | 0.49 ± 0.04 | 0.38 ± 0.07 | 0.26 ± 0.03 | 0.61 ± 0.11 |
| Muscle | 11.96 ± 1.56 | 26.79 ± 7.14 | 21.88 ± 2.74 | 18.56 ± 2.34 | 29.70 ± 2.56 |
| Lung | 2.85 ± 0.52 | 1.65 ± 0.11 | 1.17 ± 0.06 | 0.81 ± 0.14 | 1.74 ± 0.002 |
| Kidney | 4.43 ± 0.56 | 2.21 ± 0.11 | 1.52 ± 0.28 | 1.05 ± 0.1q | 2.03 ± 0.24 |
| Spleen | 0.62 ± 0.13 | 0.44 ± 0.06 | 0.36 ± 0.04 | 0.23 ± 0.04 | 0.06 ± 0.07 |
| Liver | 21.23 ± 2.66 | 16.16 ± 4.71 | 10.12 ± 1.26 | 7.54 ± 0.77 | 13.34 ± 4.06 |
| Skin | 8.72 ± 1.52 | 9.00 ± 5.10 | 14.76 ± 4.35 | 11.22 ± 3.92 | 7.08 ± 2.33 |
| Thyroid | 0.08 ± 0.01 | 0.05 ± 0.01 | 0.07 ± 0.01 | 0.07 ± 0.05 | 0.08 ± 0.01 |
| Brain | 1.12 ± 0.15 | 0.58 ± 0.01 | 0.33 ± 0.07 | 0.18 ± 0.04 | 0.85 ± 0.12 |
| Br/Bl** | 5.51 ± 0.37 | 4.59 ± 1.10 | 3.05 ± 0.12 | 1.96 ± 0.43 | 4.10 ± 0.27 |

*Pretreated with 2 mg. of TBZ (3 minutes before [$^{123}$I]I-TBZ was injected, n = 2).
**% dose/gram ratio

| Region | Regional uptake of I-TBZ peak A | | | | |
|---|---|---|---|---|---|
| | 5 | 20 | 60 | 120 | 20* |
| Cerebellum | 0.708 ± 0.044 | 0.362 ± 0.017 | 0.225 ± 0.029 | 0.116 ± 0.026 | 0.534 ± 0.032 |
| Striatum | 0.770 ± 0.019 | 0.479 ± 0.014 | 0.271 ± 0.046 | 0.138 ± 0.022 | 0.596 ± 0.000 |
| Hippocampus | 0.725 ± 0.066 | 0.414 ± 0.032 | 0.230 ± 0.048 | 0.113 ± 0.041 | 0.581 ± 0.075 |
| Cortex | 0.792 ± 0.096 | 0.420 ± 0.031 | 0.234 ± 0.035 | 0.129 ± 0.019 | 0.585 ± 0.067 |
| Rem | 0.740 ± 0.063 | 0.395 ± 0.019 | 0.229 ± 0.036 | 0.118 ± 0.022 | 0.545 ± 0.047 |
| Str./Cb**. | 1.09 | 1.32 | 1.21 | 1.19 | 1.12 |

TABLE 4A

Biodistribution of [$^{123}$I]I-TBZ in rats (iv injection)
(% Dose/organ, Average of 3 rats ± SD)
Peak B

| Organ | Time (min.) post-injection | | | |
|---|---|---|---|---|
| | 5 | 20 | 60 | 120 |
| Blood | 4.74 ± 0.36 | 2.76 ± 0.42 | 1.89 ± 0.13 | 1.89 ± 0.34 |
| Heart | 0.63 ± 0.03 | 0.35 ± 0.02 | 0.16 ± 0.01 | 0.09 ± 0.02 |
| Muscle | 21.12 ± 1.36 | 19.78 ± 1.90 | 11.80 ± 2.02 | 5.72 ± 1.20 |
| Lung | 2.02 ± 0.22 | 1.05 ± 0.04 | 0.46 ± 0.03 | 0.27 ± 0.08 |
| Kidney | 2.18 ± 0.34 | 1.37 ± 0.11 | 0.70 ± 0.06 | 0.36 ± 0.09 |
| Spleen | 0.46 ± 0.03 | 0.28 ± 0.03 | 0.14 ± 0.03 | 0.06 ± 0.01 |
| Liver | 22.61 ± 1.85 | 17.25 ± 1.25 | 8.36 ± 1.01 | 4.35 ± 0.50 |
| Skin | 7.64 ± 3.09 | 8.37 ± 1.15 | 5.45 ± 0.64 | 4.80 ± 0.46 |
| Thyroid | 0.07 ± 0.01 | 0.05 ± 0.01 | 0.13 ± 0.03 | 0.47 ± 0.14 |
| Brain | 0.74 ± 0.07 | 0.27 ± 0.02 | 0.087 ± 0.01 | 0.042 ± 0.008 |

TABLE 4A-continued

Biodistribution of [$^{123}$I]I-TBZ in rats (iv injection)
(% Dose/organ, Average of 3 rats ± SD)

Peak B

| Organ | Time (min.) post-injection | | | |
|---|---|---|---|---|
| | 5 | 20 | 60 | 120 |
| Br/Bl** | 1.54 ± 0.16 | 1.06 ± 0.22 | 0.47 ± 0.05 | 0.25 ± 0.03 |

*Pretreated with 2 mg. of TBZ (3 minutes before [$^{123}$I]I-TBZ was injected, n = 2).
**% dose/gram ratio

| Region | Regional uptake of I-TBZ peak B | | | |
|---|---|---|---|---|
| | 5 | 20 | 60 | 120 |
| Cerebellum | 0.449 ± 0.067 | 0.162 ± 0.017 | 0.055 ± 0.005 | 0.027 ± 0.005 |
| Striatum | 0.482 ± 0.066 | 0.189 ± 0.001 | 0.062 ± 0.002 | 0.027 ± 0.003 |
| Hippocampus | 0.458 ± 0.074 | 0.189 ± 0.012 | 0.058 ± 0.009 | 0.027 ± 0.004 |
| Cortex | 0.514 ± 0.066 | 0.183 ± 0.012 | 0.060 ± 0.007 | 0.028 ± 0.005 |
| Rem | 0.465 ± 0.070 | 0.172 ± 0.011 | 0.057 ± 0.006 | 0.027 ± 0.004 |
| Str./Cb**. | 1.07 | 1.17 | 1.13 | 1.00 |

Regional brain distribution of [$^{123}$I]I-TBZ (with either a racemic mixture, peak A or B) in rats was obtained after an iv injection. By dissecting, weighing and counting samples from different brain regions (cortex, striatum, hippocampus and cerebellum), % dose/gram of the samples was calculated by comparing the sample counts with the counts of the diluted initial dose. The ratio of uptake in each region was obtained by dividing % dose/gram of each region with that of the cerebellum. The effect of tetrahydrobenazine on the uptake of peak A or peak B was investigated by pretreating the rats with the TBZ 3 mg/rat at 3 min before iv injection of [$^{123}$I]I-TBZ. At 20 min. post injection the rats were dissected and the regional brain dissection was carried out as above.

Biodistribution of a racemic mixture of [$^{123}$I]I-TBZ (2b) indicates that the compound can cross the intact blood brain barrier and localize in the brain (0.92 and 0.36% dose/organ, 2 and 30 min). The regional distribution in the rat brain (as determined by dissection method) exhibits no regional selectivity. One of the racemic mixture displayed higher brain uptake (peak A, 1.2% dose/organ, 2 min) and significantly increased selective regional distribution.

What is claimed is:

1. A compound of the formula

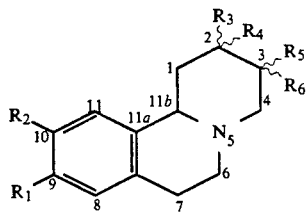

Formula I where
$R_1$ and $R_2$ are independently selected from the group consisting of H, OH, OCH$_3$, and Halogen or $R_1$ and $R_2$ can be taken together to form —O—CH$_2$—O—;
$R_3$ and $R_4$ are independently selected from the group consisting of H, OH, $C_1$-$C_{10}$ alkyl, $C_1$-$C_{10}$ alkoxy, $C_1$-$C_{10}$ alkenyloxy, —R$_7$—CH=CHI, and

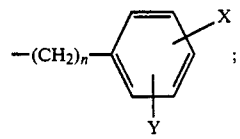

n is an integer from 0 to 5;
X and Y are independently selected from the group consisting of H, OH, OCH$_3$, Halogen and —R$_7$—CH=CHI;
$R_5$ and $R_6$ are independently selected from the group consisting of H, OH, $C_1$-$C_{10}$ alkyl, $C_1$-$C_{10}$ alkoxy, $C_1$-$C_{10}$ alkenyloxy, —R$_7$—CH=CHI, —CONR$_8$R$_9$ and

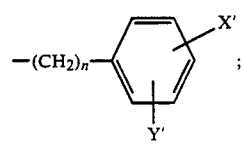

X' and Y' are independently selected from the group consisting of H, OH, OCH$_3$, Halogen, and —R$_7$—CH=CHI;
R$_7$ is selected from the group consisting of a chemical bond and $C_1$-$C_{10}$ alkyl; and
R$_8$ and R$_9$ are independently selected from the group consisting of H and $C_1$-$C_{10}$ alkyl;
provided that there is at least one iodine atom directly attached to a phenyl moiety or as part of a —CH=CHI moiety in one or more substituents selected from the group consisting of R$_3$, R$_4$, R$_5$ and R$_6$.

2. A compound of claim 1 where R$_3$ and R$_4$ are independently selected from the group consisting of H, —R$_7$—CH=CHI, OH, and OCH$_3$.

3. A compound of claim 2 where one of R$_3$ and R$_4$ is —R$_7$—CH=CHI.

4. A compound of claim 1 where R$_5$ and R$_6$ are independently selected from the group consisting of H, —R$_7$—CH=CHI, $C_1$-$C_4$ alkyl, and —CONR$_8$R$_9$.

5. A compound of claim 4 where one of R$_5$ and R$_6$ is selected from the group consisting of —CONR$_8$R$_9$ and $C_1$-$C_4$ alkyl.

6. A compound of claim 5 where $R_8$ and $R_9$ are independently selected from the group consisting of H and $C_1$-$C_4$ alkyl.

7. A compound of claim 2 where $R_5$ and $R_6$ are independently selected from the group consisting of —$R_7$—CH=CHI, $C_1$-$C_4$ alkyl, H and —$CONR_8R_9$.

8. A compound of claim 7 where one of $R_5$ and $R_6$ is selected from the group consisting of —$CONR_8R_9$ and $C_1$-$C_4$ alkyl.

9. A compound of claim 8 where $R_8$ and $R_9$ are independently selected from the group consisting of H and $C_1$-$C_4$ alkyl.

10. The compound of claim 1 which is 2-hydroxy-2-iodovinyl-3-(2-methylpropyl) -9,10-dimethoxy-1,3,4,6,7,11b -hexahydro-2H-benzo[a]quinolizine.

11. A compound of claim 1 wherein at least one iodine atom is a radioactive iodine isotope.

12. A compound of claim 2 wherein at least one iodine atom is a radioactive iodine isotope.

13. A compound of claim 3 wherein at least one iodine atom is a radioactive iodine isotope.

14. A compound of claim 4 wherein at least one iodine atom is a radioactive iodine isotope.

15. A compound of claim 5 wherein at least one iodine atom is a radioactive iodine isotope.

16. A compound of claim 6 wherein at least one iodine atom is a radioactive iodine isotope.

17. A compound of claim 7 wherein at least one iodine atom is a radioactive iodine isotope.

18. A compound of claim 8 wherein at least one iodine atom is a radioactive iodine isotope.

19. A compound of claim 9 wherein at least one iodine atom is a radioactive iodine isotope.

20. A compound of claim 10 wherein at least one iodine atom is a radioactive iodine isotope.

* * * * *